(12) United States Patent
Holmes

(10) Patent No.: US 10,420,962 B2
(45) Date of Patent: Sep. 24, 2019

(54) ORGANIC HAIR FORMULATION AND TREATMENT

(71) Applicant: Sarah Holmes, Del Mar, CA (US)

(72) Inventor: Sarah Holmes, Del Mar, CA (US)

(*) Notice: Subject to any disclaimer, the term of this patent is extended or adjusted under 35 U.S.C. 154(b) by 0 days.

(21) Appl. No.: 15/592,165

(22) Filed: May 10, 2017

(65) Prior Publication Data

US 2018/0092832 A1    Apr. 5, 2018

Related U.S. Application Data

(60) Provisional application No. 62/318,382, filed on Oct. 5, 2016.

(51) Int. Cl.

| | | |
|---|---|---|
| *A61K 8/34* | (2006.01) | |
| *A61K 8/36* | (2006.01) | |
| *A61K 8/42* | (2006.01) | |
| *A61K 8/46* | (2006.01) | |
| *A61K 8/63* | (2006.01) | |
| *A61K 8/73* | (2006.01) | |
| *A61K 8/92* | (2006.01) | |
| *A61Q 1/10* | (2006.01) | |
| *A61Q 5/02* | (2006.01) | |
| *A61Q 5/06* | (2006.01) | |
| *A61Q 5/12* | (2006.01) | |
| *A61Q 7/00* | (2006.01) | |
| *A61K 8/9789* | (2017.01) | |
| *A61K 8/9794* | (2017.01) | |

(52) U.S. Cl.
CPC ............... *A61Q 5/12* (2013.01); *A61K 8/345* (2013.01); *A61K 8/361* (2013.01); *A61K 8/42* (2013.01); *A61K 8/466* (2013.01); *A61K 8/63* (2013.01); *A61K 8/731* (2013.01); *A61K 8/922* (2013.01); *A61K 8/9789* (2017.08); *A61K 8/9794* (2017.08); *A61Q 1/10* (2013.01); *A61Q 5/02* (2013.01); *A61Q 7/00* (2013.01); *A61K 2800/5922* (2013.01); *A61Q 5/06* (2013.01)

(58) Field of Classification Search
None
See application file for complete search history.

(56) References Cited

U.S. PATENT DOCUMENTS

| | | |
|---|---|---|
| 3,590,122 A | 6/1971 | Roberts et al. |
| 5,407,675 A * | 4/1995 | Etemad-Moghadam ........ A61K 8/922 424/401 |
| 5,494,667 A | 2/1996 | Uchida et al. |
| 5,662,921 A | 9/1997 | Fein et al. |
| 5,939,059 A | 8/1999 | Franklin et al. |
| 6,193,976 B1 | 2/2001 | Porras et al. |
| 6,946,144 B1 | 9/2005 | Jordan et al. |
| 2002/0028257 A1* | 3/2002 | Catalfo ........... A61K 8/25 424/727 |
| 2006/0286062 A1 | 12/2006 | Schep et al. |
| 2010/0092582 A1* | 4/2010 | Anderson ......... A61K 8/922 424/727 |
| 2015/0374603 A1* | 12/2015 | Wu ............... A61K 8/044 514/275 |

FOREIGN PATENT DOCUMENTS

| | | |
|---|---|---|
| WO | WO9205764 A1 | 4/1992 |
| WO | WO2010137930 A2 | 12/2010 |

OTHER PUBLICATIONS

Linolenic acid, Scifinder, 2018 (Year: 2018).*

* cited by examiner

*Primary Examiner* — Susan T Tran
*Assistant Examiner* — William Craigo
(74) *Attorney, Agent, or Firm* — Meunier Carlin & Curfman LLC

(57) ABSTRACT

A leave in organic hair treatment to stimulate hair growth and reduce sebum on scalp enabling the user to apply every 12 hours without the inconvenience of build up, greasy scalp or having to wash their hair. Also, an organic hair treatment for hair growth that can be formulated separately as a shampoo composition suitable for simultaneously cleansing and conditioning human hair, comprising in combination natural and organic sourced products. Also, an organic hair treatment for hair growth that can be formulated separately as a conditioner. Also, an organic hair treatment gel for hair growth that can be formulated separately as a hair gel. Also, an organic eyelash treatment for lash growth that can be formulated separately as an eyelash conditioning treatment.

17 Claims, No Drawings

ORGANIC HAIR FORMULATION AND TREATMENT

CROSS-REFERENCE TO RELATED APPLICATION

U.S. provisional application No. 62/318,382 dated May 10, 2016 the contents of which are hereby incorporated by reference.

BACKGROUND OF THE INVENTION

The invention relates to a substantially stable liquid organic composition comprising in combination of natural and organic sourced components to stimulate hair growth and reduce sebum on the scalp. The preferred embodiments include a leave in treatment, a shampoo, a shampoo and conditioner combination, a rinse out conditioner, a styling gel and an eyelash conditioning treatment.

Shampoo compositions may be described generally as preparations comprising a surfactant or surface active material which when used under the conditions specified will remove surface grease, dirt and skin debris from the hair and scalp without adversely affecting the hair, scalp or health of the user.

Originally, shampoos were made of soap or mixtures of soaps, whereas today synthetic detergents are the primary surfactants used in the commercial products. Although soap shampoos comprising primarily either salts of C—C or salts of G-C fatty acids had the respective disadvantages of being irritating to the skin and of possessing inadequate solubility properties, shampoos, containing mixtures of salts of C—C fatty acids, e.g., olive oil soaps, were found to have outstanding cleansing and conditioning properties. To avoid the problem of insoluble soap precipitates associated with hard water, non-soap synthetic detergents were used in place of soap as the primary surfactant in shampoo compositions. While use of certain non-soap synthetic detergents resulted in enhanced foaming and cleansing action, the resultant shampoo compositions had little or no hair conditioning properties. Accordingly, it became necessary to add special expensive finishing agents such as unsaponified oils, fatty acid esters, lanolin, synthetic gums and quaternary ammonium compounds to non-soap synthetic detergent shampoos to provide the desired conditioning effects. For example, use of stearic acid as a hair conditioning acid in shampoos either tended to cause instability in liquid shampoos by separation from the liquid phase or tended to thicken the liquid shampoo U.S. Pat. No. 3,590,122 patented Jun. 29, 1971 to a non-pourable paste form. To overcome these new problems, additional expensive emulsifying agents and suspending agents were incorporated to minimize problems of physical separation of the finishing agents; or, alternatively, significant quantities of organic coupling agents were incorporated to solubilize the finishing agents.

Conditioning shampoo compositions and multi-purpose hair care products are disclosed in a number of publications. U.S. Pat. No. 5,939,059 discloses a 2-in-1 hair conditioning shampoo composition. PCT publication WO1992005764 A1 shows an improved shampoo composition comprising hair conditioners, antidandruff agents, anti-lice agents, styling agents and its mixtures. U.S. Patent publication US20060286062 A1 discloses natural shampoo and body wash composition derived from plants and natural clays. PCT publication WO2010137930 A2 shows a hair care product derived from a mixture of Rhassoul clay, natural essential oils and plant extracts. Further, the addition of the emulsifying agents, coupling agents, etc. to the shampoo compositions restricted the physical characteristics of the final products. Thus, the physical form of the final product could not be readily varied from a clear liquid to an opaque lotion without creating a host of new problems.

U.S. Pat. No. 5,494,667 February 1996 Uchida, et al. discloses a pine extract combined with a bamboo extract and/or a Japanese apricot extract effectively promotes the growth and regeneration of hair for human and animals. Administration of these compounds leads to no substantial side effects. The topically applied hair restorer containing these compounds is also effective in the prevention of alopecias, as well as in the protection of falling out of hair, dandruff, and itching of the scalp. These properties render these compounds useful in hair restorers for human and animals.

U.S. Pat. No. 5,662,921 September 1997 Fein, et al. discloses Emu oil is therapeutically used in methods for lowering cholesterol, triglycerides and low density lipoproteins and increasing high density lipoproteins; preventing and treating allergies; preventing scarring; treating headaches; preventing nose bleeds; treating and preventing cold and flu symptoms; and relieving discomfort associated with menstruation. Additionally, emu oil acts as an effective chemical buffer in combination with glycolic acid.

U.S. Pat. No. 6,193,976 February 2001 Porras, et al. discloses methods for the treatment and/or prevention of hair loss and methods for the regeneration or restoration of hair growth comprising a step of identifying an individual suffering from or susceptible to hair loss or hair thinning or in need of hair regeneration, and a step of administering an extract of the root of a Vetiver grass.

U.S. Pat. No. 6,946,144 September 2005 Jordan discloses a transdermal delivery system that can deliver high molecular weight pharmaceuticals and cosmetic agents to skin cells.

The present invention focuses on safe natural and organic components to treat hair growth.

The above referenced patents and patent applications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Although various hair treatment is known to the art, all, or almost all of them suffer from one or more than one disadvantage. Therefore, there is a need to provide an organic hair treatment and formulation.

SUMMARY OF THE INVENTION

The present invention relates in general to various embodiments for hair treatment and hair growth as well as reducing sebum at the scalp to enable the user to use every 12 hours without build-up, greasy scalp or having to wash their hair.

An object of the present invention is to make organic or natural hair growth stimulation formulas that also reduce sebum at the scalp to enable the user to use every 12 hours without build-up, greasy scalp or having to wash their hair.

An object of the present invention is to make healthy hair products that are more effective at fighting hair thinning and hair loss than prescription products and without the side effects that prescription products have. The present invention stimulates hair growth and reduces sebum on the scalp and is not currently available on the market other than by Hébé Healthy Hair.

An object of the present invention is to customize formulations for different applications, for example, hair on the head and eyelashes.

An object of the present invention is to have formulations that can be used quickly, for example a leave in treatment that can be used on dirty hair to refresh scalp and stimulate growth at the same time. Most hair stimulating products come in a shampoo or conditioner form that can be applied and must be rinsed away during a normal shower period. Or products are leave in serums that weigh down the hair, make it greasy and/or dry and cause breakage. Hébé Healthy Hair believes that the key to fighting hair loss is by applying the product every 12 hours on the scalp. The leave in treatment of the present invention allows users to do just that. Hébé Healthy Hair believes that it is important to keep all of the hair healthy while treating hair loss.

Another object of the present invention is to have formulations that are left in the hair so that the active ingredients in the formulation can have maximum exposure to the skin.

BRIEF DESCRIPTION OF THE FIGURES n/a

DETAILED DESCRIPTION

The present invention relates in general to:

Organic Aloe Leaf Juice may reduce inflammation, increase circulation, eliminate sebum and dandruff, unclog hair pores, keep scalp and hair moisturized, and balance pH level of scalp.

Hydroxyethylcellulose is a gelling and thickening agent used in cosmetics derived from cellulose.

Glycerin is a colorless, scentless, thick liquid found in cosmetics. It has anti-microbial properties. Glycerin comes from natural or synthetic sources. Our formula is derived from natural Palm Oil. Glycerin is heavy in humectants, which pull moisture into the hair and retain it.

Organic Borage Oil contains a fatty acid called Gamma Linolenic Acid. GLA has anti-inflammatory effects. It improves water retention to make the skin and hair supple and hydrated. It also dissolves sebum, so it helps combat oily skin and hair. It may also acts as a DHT blocker.

Alpha Linolenic Acid is an essential omega-3 fatty acid. It is called "essential" because it is needed for normal human growth and development but our bodies do not produce it. It may also acts as a DHT blocker.

Gamma Linolenic Acid is an essential omega-6 fatty acid, which the body needs for normal human growth. Our body can convert to substances that reduce inflammation and cell growth. It may also acts as a DHT blocker.

Beta Sitosterol may reduce inflammation and is a substance found in plants, fruits, vegetables, nuts, and seeds. It may help reduce cholesterol levels by limiting the amount of cholesterol that is able to enter the body. It may also acts as a DHT blocker.

Methylsulfonylmethane (MSM) is marketed as a dietary supplement. It is a naturally occurring sulfur compound found in tissues of all plants and animals. It keeps the body properly pH balanced. It must be present for collagen formation. It may reduce inflammation.

Pro Vitamin B5 (Panthenol) is a natural, hydrating form of vitamin B. It is used in many beauty products. It has absorption properties that make it an excellent moisturizer and emollient. Panthenol's ability to penetrate, help it improve damaged hair, reduce split ends, and add shine to hair.

Organic Rosemary Extract is part of the mint family. It may reduce inflammation and block DHT.

Organic Sunflower Oil is packed with vitamins A, B, C, E, potassium, iron, and calcium that are all beneficial for hair. It contains high levels of omega-9 fatty acid, which may be responsible for preventing brittle hair and hair loss. May act as a sunscreen and protects from UV lights.

Organic Green Tea Extract may increase circulation and have anti microbial properties. By increasing the activity of white blood cells and acting as an antioxidant, green tea is thought to protect your body against toxins and other potentially harmful agents that cause cellular damage and disease.

Organic Nettle Leaf Extract may reduce inflammation, enhance responses of the immune system, and reduce allergy symptoms. It may tighten skin, reduce sebum, relive irritation, improve firmness, and reduce dandruff. It may also act as a DHT blocker.

Organic Skullcap Extract is a type of mint. It has the following properties associated with it: anti-oxidant, anti-inflammatory, anti-bacteria, and anti-histamine.

Saw Palmetto (Extract) "is the most popular herbal hair loss treatment, although it does not have the approval of the U.S. Food and Drug Administration or large-scale scientific studies to back its use for hair loss.

Its popularity among hair-loss sufferers rests in its supposed similarities to Finasteride as a treatment for enlarged prostates. Proscar, which is a 5 mg Finasteride tablet, is used to treat enlarged prostates, while Propecia, which is 1 mg of Finasteride, is used to treat hair loss.

As of 2011, Minoxidil and Finasteride were the only two hair-loss treatments approved by the FDA. Many over-the-counter hair-loss treatments, such as Provillus, include Minoxidil packaged with other treatments in order to claim FDA approval, although the only approved item in the package is Minoxidil. The lack of an FDA approval does not mean saw palmetto will not work as a hair-loss treatment, only that it has not been shown to work in clinical settings. It is unlikely saw palmetto will ever receive FDA approval, as it is not patented and it typically costs millions of dollars to conduct the tests the FDA requires."

Pumpkin Extract is packed with vitamins A, K, B (Biotin), E, sulfur, selenium, zinc and omega-3 fatty acids. It may improve the immune system and lower cholesterol levels. Zinc and selenium protect against environmental pollution and UV rays. Vitamin A might aid in the formation of new cells and increase circulation. Vitamin E may act as an anti-oxidant. Pumpkin seed may also acts as a DHT blocker.

Evening Primrose Extract contains a high concentration of a fatty acid called GLA and it is this fatty acid that is largely responsible for the remarkable healing properties of the plant.

Linseed Extract is rich in alpha linolenic acid (ALA) an omega-3 fatty acid.

Organic Alcohol used as a vehicle to deposit the ingredients on the hair and assist in preserving.

Phenoxyethanol also known as Ethylene Glycol Monophenyl Ether, is a mild agent. Its primary use is as a preservative in cosmetics and beauty products but it can also be found naturally in green tea. However, the commercial ingredient is created in a lab. It has become a widely used ingredient because in a very low concentration (less than 1%) it is considered non-irritating, gentle and it does not release formaldehyde. The CIR has approved it for use as a preservative because of its ability to kill bacteria and stabilize formulas—this makes the products safe to use. Phenoxyethanol is approved worldwide (including Japan and EU) for use in all types of cosmetics, up to a 1% concentration.

Alternative preservatives include parabens and formaldehyde-releasing chemicals, both of these show evidence of potential health risks.

Many tests have been done and when guidelines are met (less than 1% concentration) the preservative is safe for use and it is actually making the product safer. The lab that we use to create our products stands behind its formulations and the use of phenoxyethanol as a preservative agent.

Phenoxyethanol is the best and healthiest mild preservative agent available.

Tetrasodium EDTA decreases the reactivity of metal ions in a product. This makes hard water "soft." Hard water affects the way our hair reacts to products. Tetrasodium EDTA improves the quality of hair product efficacy.

Jojoba oil is unique in that, unlike most other vegetable oils, it closely resembles sebum, a waxy substance produced by our skin glands, so it can act as a natural skin conditioner. It has nearly replaced animal fats in the manufacture of skin lotions and creams.

How Jojoba oil controls hair loss is by helping the follicles grow new hair. There are sebaceous glands inside each hair follicle. As the hair shaft grows out of the follicle, it carries a coating of sebum that protects the hair. The sebum and other debris can sometimes clog the follicle, preventing the smooth growth of the hair.

Jojoba oil can easily seep into the follicles and dissolve the sebum buildup, clearing up the blockage and facilitating the growth of new hair. The vitamins and minerals in the oil can nourish the skin and improve the overall health of the scalp.

Applying Jojoba oil to dry and frizzy hair can help moisturize and condition the hair, making it more manageable and tangle free. Apply the oil to the hair before wash or along with shampoo. This prevents the shampoo from stripping off the natural oil in the hair. You can also apply some Jojoba oil when the hair is still damp from a hair wash. The oil can form a thin waxy coating on each hair shaft, protecting it from the dust and dryness.

Biotin may increase the elasticity of hair and prevent breakage.

Vitamin C (and/or Asorbic Acid) has anti-oxidant properties that may protect your hair from aging. It may also protect your hair from minerals and chlorine found in your water. It also may assist in the production of collagen.

Sea Kelp is a rich source of iodine, minerals, and amino acids. It contains calcium, zinc, potassium, magnesium, iron, folate, vitamins A, B's and K, which are all helpful in promoting a healthy head of hair.

Marine Collagen in our formula is made from tilapia. It is a natural rejuvenating source that may delay the aging process by improving the body's ability to rebuild cells and make it more resistant to environmental toxins and free radicals. Collagen makes up approximately 30% of our body's total protein. As we age, our collagen levels decrease.

Exemplary Embodiments

Leave in Serums "Grow—Youth Nectar No 1", "Grow—Black Label Maximum Results for Fine Hair"

The hair care composition of the present invention comprises the following ingredients in referred quantity according to an exemplary embodiment.

| Ingredient | Percent Weight |
|---|---|
| Aloe Leaf Juice or Water | 0.01-98.0 |
| Hydroxyethylcellulose - thickener | 0.01-5.0 |
| Glycerin - thickener | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Phenoxyethanol | 0.01-5.0 |
| Ethylenediaminetetraacetic acid (EDTA) | 0.01-5.0 |
| Organic Alcohol - 95% ethanol and 5% water | 0.01-5.0 |

Leave in Serum "Grow—Black Label Nectar—Maximum Results for Coarse Hair"

The hair care composition of the present invention comprises the following ingredients in referred quantity according to an exemplary embodiment.

| Ingredient | Percent Weight |
|---|---|
| Aloe Leaf Juice or Water | .01-98.0 |
| Hydroxyethylcellulose - Thickener | 0.01-5.0 |
| Glycerin - Thickener | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Phenoxyethanol | 0.01-5.0 |
| Ethylenediaminetetraacetic acid (EDTA) | 0.01-5.0 |
| Organic Alcohol - 95% ethanol and 5% water | 0.01-5.0 |
| Biotin | 0.01-5.0 |
| Vitamin C | 0.01-5.0 |
| Sea Kelp | 0.01-5.0 |
| Marine Collagen | 0.01-5.0 |

Leave in Serum "Smooth—Youth Nectar No 2"

The hair care composition of the present invention comprises the following ingredients in referred quantity according to an exemplary embodiment.

| Ingredient | Percent Weight |
|---|---|
| Aloe Leaf Juice or Water | 0.01-98.0 |
| Hydroxyethylcellulose - Thickener | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |

| Ingredient | Percent Weight |
| --- | --- |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Phenoxyethanol | 0.01-5.0 |
| Ethylenediaminetetraacetic acid (EDTA) | 0.01-5.0 |
| Organic Alcohol | 0.01-5.0 |
| Biotin | 0.01-5.0 |
| Vitamin C | 0.01-5.0 |

Leave in Serum "Nourish—Youth Nectar No 3"

The hair care composition of the present invention comprises the following ingredients in referred quantity according to an exemplary embodiment.

| Ingredient | Percent Weight |
| --- | --- |
| Aloe Leaf Juice or Water | 0.01-98.0 |
| Hydroxyethylcellulose - Thickener | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Phenoxyethanol | 0.01-5.0 |
| Ethylenediaminetetraacetic acid (EDTA) | 0.01-5.0 |
| Organic Alcohol | 0.01-5.0 |
| Biotin | 0.01-5.0 |
| Vitamin C | 0.01-5.0 |
| Sea Kelp | 0.01-5.0 |
| Marine Collagen | 0.01-5.0 |

Shampoo

The hair care composition of the present invention comprises the following ingredients in referred quantity according to an exemplary embodiment.

| Ingredient | Percent Weight |
| --- | --- |
| Aloe Leaf Juice or water | 0.01-75.0 |
| Lauryl Glucoside | 0.01-25.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Caprylhydroxamic Acid (and) Glyceryl Caprylate (and) Glycerin | 0.01-5.0 |
| Tetrasodium Glutamate Diacetate | 0.01-5.0 |
| Organic Alcohol | 0.01-5.0 |
| Biotin | 0.01-5.0 |
| Vitamin C | 0.01-5.0 |
| Sea Kelp | 0.01-5.0 |
| Marine Collagen | 0.01-5.0 |
| Grape Seed Oil | 0.01-5.0 |
| Coconut Oil | 0.01-5.0 |

Conditioner

The hair care composition of the present invention comprises the following ingredients in referred quantity according to an exemplary embodiment.

| Ingredient | Percent Weight |
| --- | --- |
| Aloe Leaf Juice or Water | 0.01-95.0 |
| Niacin | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Hydroxyethylcellulose | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Caprylhydroxamic Acid (and) Glyceryl Caprylate (and) Glycerin | 0.01-5.0 |
| Tetrasodium Glutamate Diacetate | 0.01-5.0 |
| Biotin | 0.01-5.0 |
| Vitamin C | 0.01-5.0 |
| Marine Collagen | 0.01-5.0 |
| Grape Seed Oil | 0.01-5.0 |
| Coconut Oil | 0.01-5.0 |

Shampoo and Conditioner

The hair care composition of the present invention comprises the following ingredients in referred quantity according to an exemplary embodiment.

| Ingredient | Percent Weight |
| --- | --- |
| Aloe Leaf Juice or Water | 0.01-68.0 |
| Behentrimonium Methosulfate (and) Cetearyl Alcohol or substitute | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Lauryl Glucoside or Substitute | 0.01-28.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |

| Ingredient | Percent Weight |
| --- | --- |
| Evening Primrose Extract | 0.01-5.0 |
| Linseed Extract | 0.01-5.0 |
| Caprylhydroxamic Acid (and) Glyceryl Caprylate (and) Glycerin or substitute | 0.01-5.0 |
| Tetrasodium Glutamate Diacetate or substitute | 0.01-5.0 |
| Organic Alcohol | 0.01-5.0 |
| Biotin | 0.01-5.0 |
| Marine Collagen | 0.01-5.0 |
| Vitamin C | 0.01-5.0 |
| Grape Seed Oil | 0.01-5.0 |
| Coconut Oil | 0.01-5.0 |

Styling Gel

The hair care composition of the present invention comprises the following ingredients in referred quantity according to an exemplary embodiment.

| Ingredient | Percent Weight |
| --- | --- |
| Aloe Leaf Juice or Water | 0.01-98.0 |
| Hydroxyethylcellulose | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |
| Pumpkin Extract | 0.01-5.0 |
| Evening Primrose Extract | 0.01-5.0 |
| Linseed Extract | 0.01-5.0 |
| Sodium Phytate | 0.01-5.0 |
| Caprylhydroxamic Acid (and) Glyceryl Caprylate (and) Glycerin Or Substitute | 0.01-5.0 |
| Organic Alcohol | 0.01-5.0 |
| Biotin | 0.01-5.0 |
| Vitamin C | 0.01-5.0 |
| Sea Kelp | 0.01-5.0 |
| Marine Collagen | 0.01-5.0 |
| Grape Seed Oil | 0.01-5.0 |
| Coconut Oil | 0.01-5.0 |

Mascara Formulation for Eyelash

The hair care composition of the present invention comprises the following ingredients in referred quantity according to an exemplary embodiment.

| Ingredient | Percent Weight |
| --- | --- |
| Aloe Leaf Juice or Water | 0.01-98.0 |
| Hydroxyethylcellulose | 0.01-5.0 |
| Jojoba Oil | 0.01-5.0 |
| Borage Oil | 0.01-5.0 |
| Alpha Linolenic Acid | 0.01-5.0 |
| Gamma Linolenic Acid | 0.01-5.0 |
| Beta Sitosterol | 0.01-5.0 |
| Methylsulfonylmethane | 0.01-5.0 |
| Panthenol | 0.01-5.0 |
| Rosemary Extract | 0.01-5.0 |
| Sunflower Oil | 0.01-5.0 |
| Green Tea Extract | 0.01-5.0 |
| Nettle Leaf Extract | 0.01-5.0 |
| Skullcap Extract | 0.01-5.0 |
| Saw Palmetto (Extract) | 0.01-5.0 |

| Ingredient | Percent Weight |
| --- | --- |
| Pumpkin Extract | 0.01-5.0 |
| Evening Primrose Extract | 0.01-5.0 |
| Linseed Extract | 0.01-5.0 |
| Phenoxyethanol | 0.01-5.0 |
| Ethylenediaminetetraacetic acid (EDTA) | 0.01-5.0 |
| Organic Alcohol | 0.01-5.0 |
| Biotin | 0.01-5.0 |
| Vitamin C | 0.01-5.0 |
| Sea Kelp | 0.01-5.0 |
| Marine Collagen | 0.01-5.0 |
| Grape Seed Oil | 0.01-5.0 |
| Coconut Oil | 0.01-5.0 |

| Amino-acid (g/100 g protein) | Pure Marine Collagen (grams) |
| --- | --- |
| Alanine | 8.2-9.9 |
| Arginine | 8.7-10.0 |
| Aspartic acid | 5.0-7.0 |
| Cystin | 0 |
| Glutamic acid | 8-11.3 |
| Glycine | 20.0-25.0 |
| Histidine | 1.0-3.0 |
| Hydroxylysine | 1.0-3.0 |
| Hydroxyproline | 8.0-10.0 |
| Isoleucine | 0.5-3.0 |
| Leuicine | 2.0-4.0 |
| Lysine | 0.0-5.0 |
| Methionine | 0.8-2.0 |
| Phenylalanine | 1.0-3.0 |
| Proline | 10.0-14.0 |
| Serine | 2.5-4.5 |
| Threonine | 2.5-4.5 |
| Tryptophan | 0 |
| Tyrosine | 0.3-1.0 |
| Valine | 1.5-3.0 |

Marine Collagein is particularly rich in the following amino acids:

Hydroxyproline

A major component needed to produce collagen cells for a healthy body

Alanine

Supplies energy to muscle tissues, brain and central nervous system and strengthens immune system through its effect on antibody production Arginine Helps immune system stimulation and healing process Glycine Triggers the release of the oxygen required by the cell-making process Nut and Seed Oils are fatty acids that help provide shine, may decrease inflammation and some decrease DHT.

Sodium citrate or citric acid helps keep shampoo at the right pH balance to wash away dirt and oil while also causing hair cuticles to lie flat so hair looks shiny and smooth.

Panthenol is a form of vitamin B, it thickens hair follicles and helps to retain moisture and shine.

The purpose of a shampoo is to clean the hair. The shampoo must not clean too well, or all of the protective oils in the hair would be stripped out. The most common ingredient in shampoos is also the most common detergent in use in other products, a class of surfactants known as straight-chain alkyl benzene sulfonates. An example is Ammonium Lauryl Sulfate, or its sodium relative, or the slightly larger related molecule ammonium lauryl ether sulfate, sometimes abbreviated as ammonium laureth sulfate. These detergents work best in water that has little calcium and magnesium, as these elements bind to the detergent and make an insoluble scum. So tetrasodium EDTA is used to sequester the calcium and magnesium from the detergent, while keeping them soluble, so they rinse away without scum. Cocamide DEA (or MEA or TEA) is used as a foaming agent, to make the lather. The other surfactants will generate a certain amount of suds, but this foaming agent is added to get the amount just right. Besides its foam stabilizing effects, it is also a viscosity booster (it's thick). Another foam stabilizing detergent is PEG-5 cocamide, which is a foam stabilizer, surfactant, and emulsifier. The detergent cocamidopropyl betaine is added for several of its special properties. It is milder on the skin than the benzine sulfonates, so adding it to the mix reduces the amount of the harsher detergents needed. It is thicker than the other ingredients, so it can be added to make the mix have the right viscosity. It has anti-static properties, so the hair doesn't generate an electric charge and jump to the plastic combs and brushes used when drying the hair. It is a humectant, attracting moisture from the air, thus keeping hair from drying out. Lastly, it has antibiotic properties that can prevent spoiling of the shampoo.

The surfactant ammonium xylenesulfonate is a hydrotrope, a compound that makes it easier for water to dissolve other molecules. It is added as a thickener, and to help keep some of the odd ingredients added for marketing effect in solution, including perfumes. Glycerol stearate is another emulsifier used for this purpose. Modified cellulose based thickeners are often used, along with the surfactant based thickeners already mentioned. Glycerine is added as a humectant (draws moisture from the air), as is propylene glycol, which is also a preservative. There are many additives put in shampoos and conditioners that appear to be there mainly for marketing purposes. Honey, various herb extracts, and similar items might add to the fragrance, but are unlikely to have any effect in the concentrations used. Amino acids can act as conditioners, but the source of the amino acid is not important. Silk amino acids are no different from soy amino acids, except in the proportions of which particular amino acids are contained.

Two widely used preservatives, DMDM hydantoin and imidazolidinyl urea are found in many shampoos, to prevent fungal and bacterial spoilage. They release formaldehyde to kill germs. Another broad-spectrum biocide is isothiazolinone and the related methylisothiazolinone and methylchloroisothiazolinone. Sodium benzoate is another preservative used in shampoos. It kills bacteria, fungi, and yeasts, and works well in acidic mixtures. Another bactericide used is 2-bromo-2-nitropropane-1,3-diol.

The surface of a strand of hair is covered with overlapping sheets, somewhat like the scales on a fish, or the shingles on a house. This surface is called the cuticle. Alkaline solutions raise these scales, so they stand up. This makes the hair rougher, makes it look dull, and makes the hair shafts stick together due to the rough texture.

Most shampoos are made slightly acidic, to keep the cuticle smooth and lying flat on the hair shaft. Ingredients like citric acid are added to acidify the shampoo. As the shampoo mixes with the water in the shower or bath, or mixes with dirt on the hair, it can become less acidic as the acids mix with alkaline water or dirt. A compound that releases more acidifying ions when the acidity gets low, or absorbs acid when the acidity gets too high, is called a buffer. A typical buffering agent used in shampoo is sodium citrate. Since the goal is to keep the shampoo slightly acid, the term "pH balanced" is actually a misnomer. We want the balance to be tipped slightly to the acidic side.

Conditioners are compounds added to keep the hair cuticle smooth and slippery. Silicone oils such as dimethicone and cyclomethicone are used to make the hair shiny and slippery. Humectants (moisturizers) like panthenol help keep the cuticle moist, so that the scales do not stand up. Long chain fatty alcohols like cetyl alcohol, oleyl alcohol and stearyl alcohol lubricate the hair. One end of the molecule binds to the hair, leaving the slippery fatty end on the outside to rub against other strands of hair, or a comb. Quaternary ammonium compounds are cationic surfactants that bind well to anionic surfaces like the protein in hair. The ammonium end sticks to the hair, leaving the long fatty end of the molecule to act as a lubricant. They are slightly conductive, so the reduce the buildup of static electricity. The "quats," as they are called, include compounds like stearalkonium chloride, disteardimonium chloride, quaternium-5 or quaternium-18, polyquaternium-10 and they are all similar in form and function to cetrimonium chloride. These compounds are also widely used as fabric softeners, for all of the same reasons they make good hair conditioners. They are also used to thicken the shampoo. The emollient isopropyl palmitate is used as a skin softener, moisturizer, and as an anti-static agent.

The term organic as used herein is for descriptive purposes of the preferred source of the compound; however, the term organic is not intended to limit the source of a described compound. For example, if a synthetic skullcap could be synthesized in a laboratory it is possible to use that as a substitute compound.

While the foregoing description sets forth various examples and details relating to preferred embodiments, it should be appreciated that the description is illustrative only and should not to be construed as limiting the invention. Thus, the scope of this disclosure is not to be limited by the illustrations or the foregoing descriptions thereof, but rather solely by the appended claims.

What is claimed is:

1. A hair treatment comprising
   0.01-98.0 weight percent of either Aloe Leaf Juice or Water,
   0.01-5.0 weight percent Hydroxyethylcellulose,
   0.01-5.0 weight percent of either Glycerin or Jojoba Oil,
   0.01-5.0 weight percent Borage Oil,
   0.01-5.0 weight percent Alpha Linolenic Acid,
   0.01-5.0 weight percent Gamma Linolenic Acid,
   0.01-5.0 weight percent Beta Sitosterol,
   0.01-5.0 weight percent Methyl sulfonylmethane,
   0.01-5.0 weight percent Panthenol,
   0.01-5.0 weight percent Saw Palmetto,
   0.01-5.0 weight percent Evening Primrose,
   0.01-5.0 weight percent Nettle Leaf Extract, and
   0.01-5% Skullcap Extract.

2. The hair treatment of claim 1, further comprising 0.01-5% Rosemary Extract by weight.

3. The hair treatment of claim 1, further comprising 0.01-5% Sunflower Oil by weight.

4. The hair treatment of claim 1, further comprising 0.01-5% Green Tea Extract by weight.

5. The hair treatment of claim 1, further comprising 0.01-5% Pumpkin Extract by weight.

6. The hair treatment of claim 1, further comprising 0.01-5% Linseed Extract by weight.

7. The hair treatment of claim 1, further comprising 0.01-5% Phenoxyethanol by weight.

8. The hair treatment of claim 1, further comprising 0.01-5% Ethylenediaminetetraacetic acid by weight.

9. The hair treatment of claim 1, further comprising 0.01-5% Biotin by weight.

10. The hair treatment of claim 1, further comprising 0.01-5% Vitamin C by weight.

11. The hair treatment of claim 1, further comprising 0.01-5% Sea Kelp by weight.

12. The hair treatment of claim 1, further comprising 0.01-5% Marine Collagen by weight.

13. The hair treatment of claim 1, further comprising 0.01-5% Caprylhydroxamic Acid and Glyceryl Caprylate by weight.

14. The hair treatment of claim 1, further comprising 0.01-5% Glycerin by weight.

15. The hair treatment of claim 1, further comprising 0.01-5% Jojoba by weight.

16. The hair treatment of claim 1, further comprising 0.01-5% Grape seed oil by weight.

17. The hair treatment of claim 1, further comprising 0.01-5% Coconut oil by weight.

\* \* \* \* \*